US00PP33428P3

(12) United States Plant Patent
Bunnik

(10) Patent No.: US PP33,428 P3
(45) Date of Patent: Aug. 31, 2021

(54) ***GUZMANIA* PLANT NAMED 'BUNGUZOR'**

(50) Latin Name: ***Guzmania* Ruiz & Pav**
Varietal Denomination: BUNGUZOR

(71) Applicant: 3B Fundus B.V., Kudelstaart (NL)

(72) Inventor: Bjorn Bunnik, Kudelstaart (NL)

(73) Assignee: 3B Fundus B.V., Kudelstaart (NL)

( * ) Notice: Subject to any disclaimer, the term of this patent is extended or adjusted under 35 U.S.C. 154(b) by 0 days.

(21) Appl. No.: 17/106,566

(22) Filed: Nov. 30, 2020

(65) Prior Publication Data

US 2021/0168984 P1 Jun. 3, 2021

(30) Foreign Application Priority Data

Nov. 30, 2019 (QZ) ..... PBR 2019/3274

(51) Int. Cl.
*A01H 5/02* (2018.01)
*A01H 6/22* (2018.01)

(52) U.S. Cl.
USPC ..... Plt./371
CPC ..... *A01H 6/225* (2018.05)

(58) Field of Classification Search
USPC ..... Plt./371
CPC ..... A01H 6/225
See application file for complete search history.

*Primary Examiner* — Anne Marie Grunberg
(74) *Attorney, Agent, or Firm* — Samuel R. McCoy, Jr.

(57) ABSTRACT

A new and distinct variety of *Guzmania* plant named 'BUNGUZOR' which is characterized by the combination of a broad, upright growth habit with foliage arranged in an attractive rosette, an inflorescence held above the foliage with small yellow flowers that are subtended by large, showy orange to red-orange floral bracts which are tipped green, and the stability of all characteristics from generation to generation.

1 Drawing Sheet

CROSS REFERENCE TO RELATED APPLICATIONS

This application claims priority to the Community Plant Variety Rights application number 2019/3274, filed Nov. 30, 2019, which is herein incorporated by reference.

Latin name of the genus and species: The Latin name of the genus and species of the novel variety disclosed herein is *Guzmania* Ruiz & Pay.

Variety denomination: The inventive variety of *Guzmania* disclosed herein has been given the variety denomination 'BUNGUZOR'.

BACKGROUND OF THE INVENTION

Parentage: The *Guzmania* variety 'BUNGUZOR' is a seedling selection which resulted from a controlled pollination breeding program. In November of 2013, the inventor performed the controlled cross-pollination of a proprietary unnamed *Guzmania* plant, the seed parent, and a second unnamed proprietary *Guzmania* plant, the pollen parent, at a commercial greenhouse in Kudelstaart, the Netherlands. Both parents were developed by the inventor and never released to the public. In June of 2016, the inventor observed one seedling from the cross which exhibited unique foliage and inflorescence characteristics and isolated the plant for further evaluation. Upon confirmation of distinctness and stability, the new *Guzmania* plant was selected for commercialization and given the name 'BUNGUZOR'.

Asexual Reproduction: 'BUNGUZOR' was first asexually propagated by way of vegetative cuttings in November of 2016 and subsequently by way of meristematic tissue culture micropropagation at a commercial tissue culture laboratory in Aalsmeer, the Netherlands. Through 6 subsequent generations, the unique features of this cultivar are stable and reproduced true to type.

SUMMARY OF THE INVENTION

The cultivar 'BUNGUZOR' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'BUNGUZOR'. These characteristics, in combination, distinguish 'BUNGUZOR' as a new and distinct *Guzmania* cultivar:

1. *Guzmania* 'BUNGUZOR' exhibits a broad, upright growth habit with foliage arranged in an attractive rosette; and
2. *Guzmania* 'BUNGUZOR' exhibits dark green foliage which is slightly twisted; and
3. *Guzmania* 'BUNGUZOR' exhibits a relatively large terminal spike inflorescence held above the foliage; and
4. *Guzmania* 'BUNGUZOR' exhibits an inflorescence with small yellow flowers that are subtended by large, showy orange to red-orange floral bracts which are tipped green.

BRIEF DESCRIPTION OF THE FIGURES

FIG. 1 illustrates, as nearly true as it is reasonably possible to make the same in color photographs of this type, an exemplary plant of 'BUNGUZOR' grown in a commercial greenhouse in Kudelstaart, the Netherlands. This plant is approximately 7 months old, shown planted in a 12 cm container.

BOTANICAL DESCRIPTION OF THE PLANT

The following observations and measurements, made in November of 2020, describe averages from a sample set of six specimens of 7 month-old 'BUNGUZOR' plants grown in 12 cm nursery pots at a commercial greenhouse in Kudelstaart, the Netherlands. Plants were grown under shade cloth and maintained with a 0.8 EC fertigation program with regular overhead irrigation. No chemical pest measures were taken.

Those skilled in the art will appreciate that certain characteristics will vary with older or, conversely, with younger plants. 'BUNGUZOR' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, 2015 (sixth edition).

A botanical description of 'BUNGUZOR' and a comparison with the parent plants and most similar variety of *Guzmania* are provided below.

Plant description:

*Growth habit.*—Perennial; monopodial; broad, upright. Leaves arranged in a basal rosette, with no lateral branching, and the inflorescence growing from the center of the basal rosette and held above the foliage.

*Plant form.*—Flattened globular.

*Average height.*—17.0 cm, from the soil level to the top of the foliar plane, and 37.7 to the top of the floral plane.

*Plant spread.*—Average of 49.0 cm.

*Growth rate.*—Moderately fast.

*Plant vigor.*—Moderately vigorous.

*Propagation type.*—Vegetative cuttings and meristematic tissue culture micropropagation.

*Time to initiate roots.*—Approximately 14 to 28 days to initiate roots at 22 degrees Celsius.

*Time to produce a rooted cutting.*—Approximately 105 days at 22 degrees Celsius.

*Pest resistance and susceptibility.*—Neither resistance nor susceptibility to typical *Guzmania* pests and diseases has been observed.

*Temperature tolerances.*—USDA Zones 10 to 13; at least tolerant of temperatures to 40 degrees Celsius. High tolerance to rain inundation; high tolerance to wind.

Root system:

*General.*—Thick; medium density.

*Texture.*—Slightly fleshy.

Foliage:

*Arrangement.*—Basal rosette. No stems or lateral branches.

*Attachment.*—Sessile.

*Division.*—Simple.

*Quantity of leaves.*—18.

*Lamina.*—Dimensions — 35.8 cm long and 3.5 cm wide. Thickness — Approximately 0.9 cm. Shape of blade — Ensiform. Aspect — Moderately concave. Attitude — Upright and moderately reflexed. Apex — Apiculate. Base — Sheathing. Margin — Entire; not undulated. Pubescence, texture and luster of adaxial surface — Glabrous, smooth and moderately glossy. Pubescence, texture and luster of abaxial surface — Glabrous, smooth and moderately glossy. Color — Juvenile foliage, adaxial surface — Nearest to in between green and yellow-green, RHS 143A and 146A. Juvenile foliage, abaxial surface — Yellow-green, nearest to RHS 146B. Mature foliage, adaxial surface — Nearest to in between green and yellow-green, RHS 143A and 146A yet nearest to 146A. Mature foliage, abaxial surface — Yellow-green, nearest to RHS 146A. Venation — Pattern — Parallel. Mature foliage venation, adaxial surface — Nearest to in between green to yellow-green, RHS 137A and 146A. Mature foliage venation, abaxial surface — Yellow-green, nearest to RHS 146A.

*Sheath.*—Sheath length — 9.2 cm. Sheath width — 5.7 cm. Sheath color — Greyed-yellow, nearest to RHS 160A, and suffused with yellow-green, nearest to RHS 153A.

Inflorescence:

*Inflorescence arrangement.*—Terminal spike with showy bracts and an average of 25 flowers.

*Natural flowering season.*—Continuous flowering.

*Time to flower.*—Approximately 6 months.

*Inflorescence Quantity.*—One.

*Flowers per Inflorescence.*—Average of 25, with 10 open flower and 15 in bud stage and not opening.

*Inflorescence Height.*—Approximately 10.8 cm (measured from base of lowest flower to top of upper flower).

*Inflorescence Diameter.*—Average of 2.3 cm, excluding bracts, and 15.4 cm with bracts.

*Peduncle.*—Dimensions — Approximately 26.8 cm long and 0.7 cm in diameter. Attitude — Near vertical. Strength — Strong. Texture and luster — Glabrous, smooth, and glossy. Color — Yellow-green, RHS 145C.

Bud:

*Length.*—Average of 2.5 cm.

*Diameter.*—Average of 0.3 cm.

*Shape.*—Lanceolate.

*Texture and luster.*—Glabrous, smooth, and moderately glossy.

*Color.*—Yellow, nearest to RHS 4D; distal one-third portion and base are darker, nearest to RHS 7B.

Flower:

*Flower type and form.*—Single; oblanceolate to narrow oblong.

*Attachment.*—Sessile.

*Attitude.*—Upright.

*Height.*—Approximately 0.2 cm.

*Diameter.*—Average of 0.3 cm.

*Depth.*—Approximately 2.7 cm.

*Fragrance.*—No fragrance.

*Lastingness.*—4 weeks.

*Persistent.*—Persistent.

*Petals.*—Quantity of Petals — 3. Arrangement — Rotate; single whorl; petals free. Length — Approximately 1.0 cm. Width — Approximately 0.3 cm. Shape — Oblong Aspect — Concave. Apex — Obtuse. Base — Cuneate. Margin — Entire; not undulated. Pubescence, texture and luster of upper surface — Glabrous, smooth and slightly glossy. Pubescence, texture and luster of lower surface — Glabrous, smooth and slightly glossy. Color when opening, upper surface — Yellow, nearest to RHS 4A; apex is darker, nearest to RHS 7A. Color when opening, lower surface — Yellow, nearest to RHS 2A; apex is yellow-orange, nearest to RHS 14B. Color when fully opened, upper surface — Yellow, nearest to RHS 4A; apex is darker, nearest to RHS 7A. Color when fully opened, lower surface — Yellow, nearest to RHS 4A; apex is darker, nearest to RHS 7A. Fading, upper surface — Not fading. Fading, lower surface — Not fading. Venation color, fully opened, upper surface — No venation is visible. Venation color, fully opened, lower surface — No venation is visible.

*Calyx.*—Shape — Rotate. Length — Average of 2.5 cm. Diameter — Average of 0.45 cm.

*Sepals.*—Quantity — 3 unfused sepals in a single whorl. Arrangement — Rotate. Length — 2.2 cm. Width — 0.3 cm. Shape — Lanceolate. Aspect — Strongly concave. Apex — Bluntly acute. Base — Cuneate. Margin — Entire. Pubescence, texture and luster of upper surface — Glabrous, smooth, and moderately glossy. Pubescence, texture and luster of lower surface — Glabrous, smooth, and moderately glossy. Color when opening, upper surface — Translucent white, nearest to in between 155C and N155A, and suffused with yellow towards the apex, nearest to RHS 8C. Color when opening, lower surface — Translucent white, nearest to in between 155C and N155A, and suffused with yellow towards the apex, nearest to a mixture of RHS 8B and 8C. Color when fully opened, upper surface — Translucent white, nearest to in between 155C and N155A, and suffused with yellow towards the apex, nearest to RHS 8C. Color when fully opened, lower surface — Translucent white, nearest to in between 155C and N155A, and suffused with yellow towards the apex, nearest to a mixture of RHS 8B and 8C.

*Bract.*—General — One large, colorful bract at the base of each individual flower. Shape — Obovate to oblong. Aspect — Concave. Dimensions — Average of 8.8 cm long, including the sheath, and 2.8 cm wide. Apex — Apiculate. Base — Sheathing. Margins — Entire. Texture and luster, upper surface — Smooth and moderately glossy. Texture and luster, lower surface — Smooth and moderately glossy. Upper bract color, upper surface — Nearest to a mixture of orange and orange-red, RHS N25B and 33B; fading to a mixture of red and brown towards the apex, nearest to RHS 42A and 200B; tip is yellow-green, nearest to RHS 147A. Upper bract color, lower surface — Nearest to orange-red, RHS N30A and N30B; fading to red towards the apex, nearest to RHS 42B, and suffused with yellow-green, RHS 147A, towards the tip; tip is yellow-green, nearest to RHS 147A. Lower bract color, upper surface — Green, RHS 137B, and suffused with red at the base and margins, nearest to a mixture of RHS 42B and 42C. Lower bract color, lower surface — Green, RHS 138A, and suffused with red at the base and margins, nearest to RHS 42B. Sheath — Sheath length — Average 4.4 cm. Sheath width — Average 4.3 cm. Sheath color, upper surface — Nearest to in between yellow-green and greyed-green, RHS 152D and 160A. Sheath color, lower surface — Yellow-green, nearest to in between RHS N144A and 151A. Venation — No venation is visible.

Reproductive organs:

*Stamens.*—Quantity — 6, on average. Anthers — Attachment — Dorsifixed. Shape — Narrow sagitate. Dimensions — Average of 0.55 cm long and 0.075 cm wide. Color — White, nearest to RHS 155A. Filaments — Length — 0.3 cm, on average. Color — White, nearest to RHS 155D. Pollen — None detected.

*Pistil.*—Quantity — 1. Length — 0.45 cm. Style — Length — 0.35 cm. Color — White, nearest to RHS 155D. Stigma — Shape — Club-shaped. Dimensions — Average of 0.1 cm long and 0.1 cm wide. Color — Yellow, nearest to RHS 4D. Ovary Color — Yellow-green, nearest to RHS 150D.

Fruit and seed: To date, not observed.

Comparisons with the parent plant: Plants of the new cultivar 'BUNGUZOR' differ from its seed parent, an unnamed proprietary *Guzmania* plant, by the characteristics described in Table 1.

TABLE 1

| Characteristic | 'BUNGUZOR' | The seed parent |
|---|---|---|
| Foliage length. | Shorter than the seed parent. | Longer than 'BUNGUZOR'. |
| Foliage attitude. | Upright and reflexed. | Upright and not reflexed. |
| General coloration of the bracts. | Orange to orange-red, generally appearing as more of a dull orange. | More of a bright orange coloration. |
| Inflorescence size. | Larger than the seed parent. | Smaller than 'BUNGUZOR'. |

Plants of the new cultivar 'BNGUZOR' differ from its pollen parent, an unnamed proprietary *Guzmania* plant (not patented), by the characteristics described in Table 2.

TABLE 2

| Characteristic | 'BUNGUZOR' | The pollen parent |
|---|---|---|
| Foliage length. | Longer than the pollen parent. | Shorter than 'BUNGUZOR'. |
| General coloration of the bracts. | Orange to orange-red, generally appearing as more of a dull orange. | More of a bright orange coloration. |
| Inflorescence size. | Larger than the pollen parent. | Smaller than 'BUNGUZOR'. |

Comparison with the most similar *Guzmania* cultivar known to the inventor: 'BUNGUZOR' is similar in many horticultural characteristics to the commercial cultivar *Guzmania* 'Variada' (Community Plant Variety Rights grant number 42943). However 'BUNGUZOR' differs from 'Variada' by the characteristics described in Table 3.

TABLE 3

| Characteristic | 'BUNGUZOR' | 'Variada' |
|---|---|---|
| Length of foliage. | Longer than 'Variada'. | Shorter than 'BUNGUZOR'. |
| Foliage attitude. | Upright and reflexed. | Upright and not reflexed. |
| General coloration of the floral bracts. | Orange to orange-red, generally appearing as more of a dull orange. | More of a bright orange coloration. |
| Inflorescence size. | Larger than 'Variada'. | Smaller than 'BUNGUZOR'. |

That which is claimed is:

1. A new and distinct variety of *Guzmania* plant named 'BUNGUZOR', substantially as described and illustrated herein.

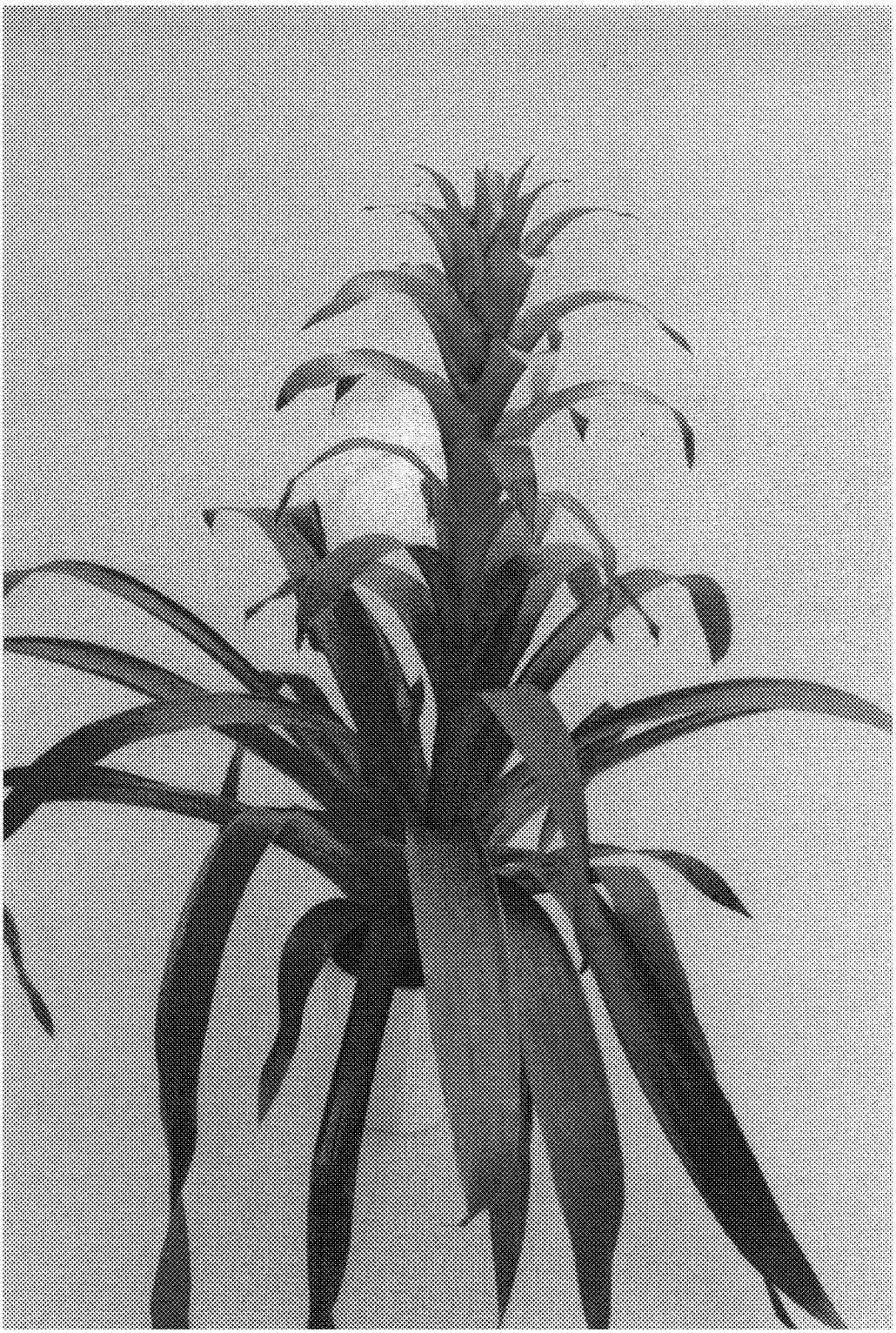

* * * * *